United States Patent [19]

Uddo Jr. et al.

[11] Patent Number: 4,735,615
[45] Date of Patent: Apr. 5, 1988

[54] CHOLANGIOCLAMP

[76] Inventors: Joseph F. Uddo Jr., 1201 Ridgelake Dr., Metairie, La. 70001; John R. Breaux, 327 Bonnabel Blvd., Metairie, La. 70005

[21] Appl. No.: 17,865
[22] Filed: Feb. 24, 1987
[51] Int. Cl.⁴ .............................................. A61M 25/00
[52] U.S. Cl. .................................... 604/178; 128/346; 128/DIG. 26
[58] Field of Search ............... 604/178, 174, 177, 179; 128/DIG. 26, 346; 285/325, 326, 242–244; 24/17 B, 17 AP, 129

[56] References Cited

U.S. PATENT DOCUMENTS 2,729,876  1/1956  Hagemann ..................... 604/174 X
3,814,080  6/1974  Norman .......................... 604/174
4,484,911  11/1984  Berlin et al. ................. 128/DIG. 26

Primary Examiner—Stephen C. Pellegrino
Attorney, Agent, or Firm—Alexander F. Norcross

[57] ABSTRACT

A clamp for connecting and securing a catheter in position within a tubular structure has a positioning ring and support member to align and slidingly affix the clamp along the catheter and includes a split toothed plastic clamping ring which may be expanded by the application of forceps to enclose the catheter and a section of the tubular structure into which the catheter is inserted and, when released, forms a toothed occlusal seal, enclosing with mild pressure the tubular structure between the clamp and the catheter. The clamp is designed to permit the insertion and securing of a catheter into an opening cut along the length of the tubular structure, by providing a passage or gap for the passage of the distal portion of the tubular structure.

2 Claims, 2 Drawing Sheets

CHOLANGIOCLAMP

BACKGROUND OF THE INVENTION

This invention relates to an apparatus for securing a catheter in position for insertion into a tubular body member or structure.

The invention may best be described by reference throughout to the procedure and use of the device in reference to the operative procedure of intraoperative cholangiography. Cholangiography is a procedure to determine the presence or absence of gall stones in the common bile duct. It is commonly required during gall bladder surgery where positive indications of gall stones are found and where it becomes necessary to determine the presence of or absence of gall stones in the common bile duct during the course of cholecystectomy.

The overall operative technique and its requirements are disclosed in any standard reference such as the "Textbook of Surgery", Sabiston, ed. or "Principals of Surgery" by Schwartz, et al. Only so much of the related procedure as is necessary to elucidate and illustrate the design and use of the inventive clamp will be discussed here.

In order to insure that no gall stones remain in the common bile duct, after gall bladder excision, it is now considered desirable to perform cholangiography to determine the absence of such residual gall stones should there be any evidence during gall bladder surgery that stones have been formed; it has been estimated that in 85% of gall bladder surgery cases, cholangiography is suggested during the operative procedure.

The technique requires the placing of a catheter into the cystic duct, through a cut made in the cystic duct, and the injection, through the catheter, of radiographically opaque material. An x-ray is then obtained and examined for presence of gall stones. Upon completion of the procedure, the tube is removed and the stump of the cystic duct is tied or clipped closed.

The entire procedure is performed during the surgical operation, in order to determine the necessity of proceeding further for the removal of common bile duct stones, and thus, for the safety of the patient, must be performed accurately, expeditiously and quickly. Temporarily securing the catheter in the stump of the cystic duct has been a continuing problem. The catheter must be secured well enough to prevent leaks during dye injection, and the catheter must remain in place despite manipulation, yet the cathether must be easily removable after the x-ray is taken. Several methods have been devised, commonly all involving some form of temporary surgical tie around the cystic duct in an attempt to secure it to the catheter tip; all such techniques had attendant problems of forming a satisfactory seal to prevent the leakage of the dye without collapsing the catheter from overtightening, or of preventing the slippage of the catheter, and so as to permit rapid performance of the technique with relatively little additional trauma or strain upon the operative patient. Moreover, the use of a surgical tie is removed by cutting, and this introduces attendant dangers of laceration and injury.

SUMMARY OF THE INVENTION

The invention discloses a form of clamp, titled by the inventor the Cholangioclamp, which has been developed and is suitable for securing a catheter inserted in any tubular structure. The principal development of the clamp has been for the performance of cholangiography, however, the clamp can readily be used for other techniques such as cannulating a blood vessel or other uses as will be apparent to skilled surgeons and those with experience in the art.

The basic cholangiography catheter is similar to an Eight French or a Five French infant feeding tube; it is essentially an elongate, non-crushing, flexible plastic tube, of a material suitable for gas sterilization, fluidly connected through a Leur lock to a source of radiographically opaque dye under pressure.

The inventive clamp consists of an elongate structure having a positioning ring, slidably engaging the catheter tube, fixed at one edge of a support bridge, which extending along the catheter tube, terminates in a split ring clamp encompassing catheter and duct. The clamp is a relatively thick split cylinder clamp resembling a split ring of a flexible resilient material. The clamp section has a radial gap dividing it into two clamping semi-cylinders which have an internally toothed aspect. The entire clamp is made of a flexible, gas sterilizable thermosetting plastic or any similar resilient material with physical memory. A hinge point about which the semi-cylinder or disk sections rotate to open or close the gap is provided by notching a section of the inner cylindrical tooth surface at a point opposite the gap; two angled opposing cleats extend radially outward from the cylindrical clamp and are adapted to be grasped by forceps for the application of squeezing force.

The clamp is actuated by squeezing the cleats or gripping them with forceps which rotates the two disc halves of the clamping cylinder open at the gap due to the action of the notched hinge point. The gap may be opened wide enough to encompass both an enclosed tubular structure, such as a cystic duct, and an inserted catheter tip. When the forceps are released the spring action of the disc material closes the two semi-cylinder members upon the tubular structure and the catheter tip, grasping the tubular member in the provided tooth surface providing an occlusal, pressure resistant seal against the catheter.

Dye is then inserted in a manner well understood in the art; the supporting ring and support bridge hold the clamp and the catheter tube in alignment with the tubular member, maintaining a steady, even but non-damaging pressure.

At the conclusion of the technique forceps may then be applied to the cleats, opening the gap and permitting the removal of clamp/catheter unit. The catheter may be removed by sliding from the duct.

It will be found that the clamp of the described invention is easily manipulated, and by its elongate retention of the catheter, aids in the alignment and insertion of the catheter within the cystic or common bile duct or similar tubular structure. The construction as disclosed provides an easy and repeatable pressure seal, significantly speeding and easing the performance of the desired operative technique.

It is thus an object of this invention to provide a clamp structure readily used under surgical conditions for clamping a catheter to within a tubular body structure.

It is a further object of this invention to provide a readily positionable clamping structure for use in conjunction with a catheter and a tubular body structure to maintain the catheter in optimum alignment with the tubular body structure.

It is a further object of this invention to provide a readily applicable catheter clamp which provides a repeatable, non-damaging pressure seal for the prevention of leakage of liquid injected by catheter to within a tubular body structure.

These and other advantages of the invention will be apparent to those skilled in the art from the detailed description of the preferred embodiment which follows.

DETAILED DESCRIPTION OF THE PREFERRED EMBODIMENT

The overall surgical and operative procedures involved in gall bladder surgery, including cholangiography, are well described in the surgical literature, including the references above shown and are incorporated herein by reference.

Figure 1:
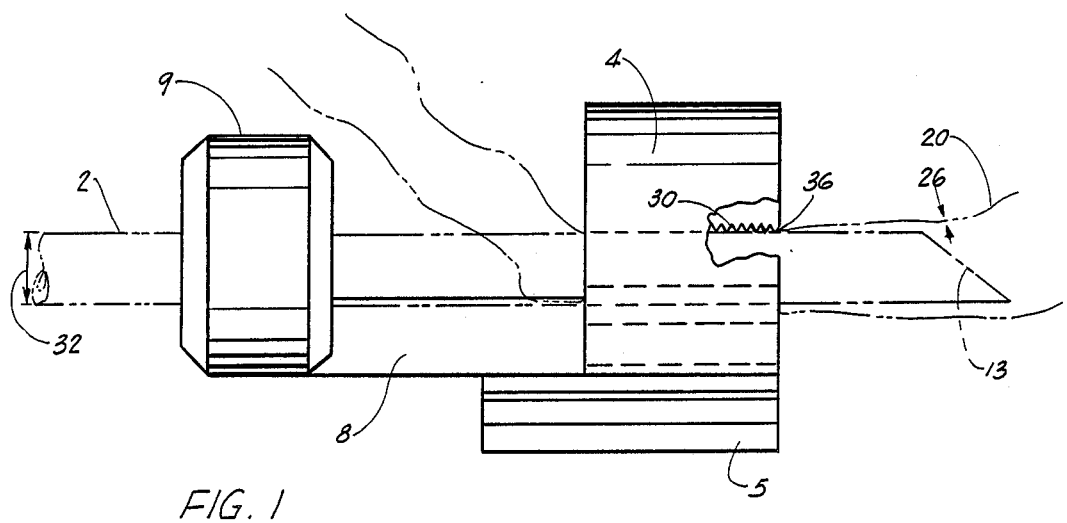
FIG. 1 is a side view showing the clamp of the current invention in operative engagement with a catheter inserted within a common bile duct.
Figure 2:
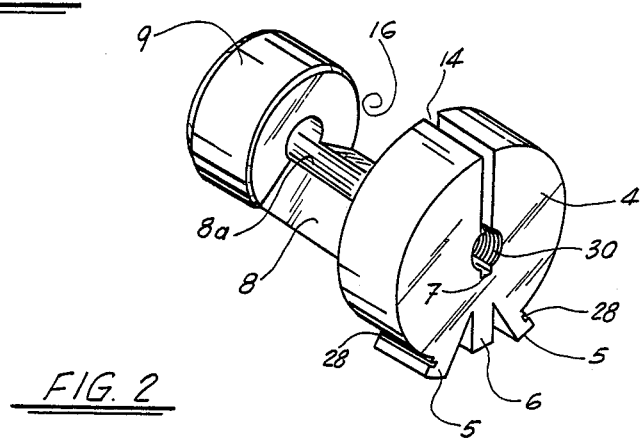
FIG. 2 is an angled side view of the clamp of the current invention.
Figure 3:
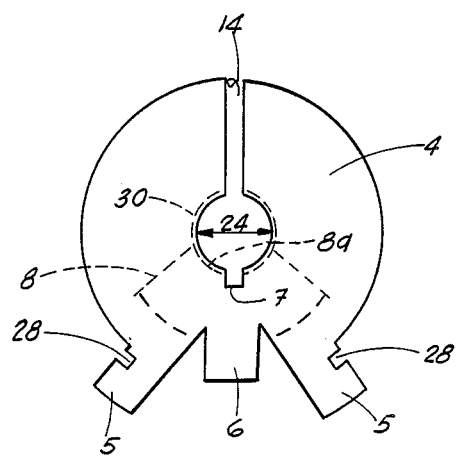
FIG. 3 is an end view of the clamp, viewed from the direction of the catheter tip.
Figure 4:
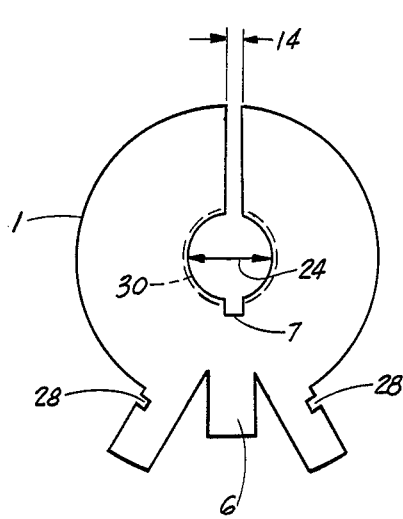
FIG. 4 and FIG. 4a are end views of the clamp of the current invention showing the operative actuation of the clamp.
Figure 4A:
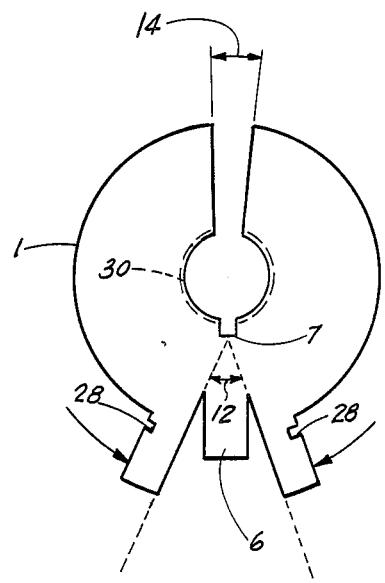

Referring to the figure, especially FIG. 2, the invention or clamp is shown as comprising a relatively thick sliding ring structure 9, adapted for circumferentially and slidably engaging a provided catheter 2. Ring 9 is supported upon an angled support bridge 8, having a curved upper surface 8a adapted for sliding engagement with the outer circumference of catheter 2 and descending at essentially in a 90° arc or as a one quarter radial section coaxial with the outer circumference of ring 9.

Mounted on an end of support bridge 8, opposite to that of ring 9 is notched clamping section 4. Notched clamping section 4 comprises a flexible relatively thick disc section, made of a sterilizable material which is flexible but maintains a memory, and does not, thereby, permanently deform. The entire invention should be of radiolucent material, so as not to obscure the x-ray of the cystic duct area. It has been found that general thermosetting plastic, such as polyethylene and its derivatives, are adequate materials for the construction of the clamp.

The clamp disc 4 is divided into two halves by radial notch gap 14, extending diametrically opposite to the positioning of support bridge 8. A central, cylindrical passage is provided within disc 4, adapted to the passage of catheter 2 and provided with an interior toothed surface 30, which in the preferred embodiment are repeated teeth having a pitch of approximately 0.5 millimeters per tooth. Within tooth gripping surface 30, and at a point opposite to radial gap 14, is found pivot notch 7, which has been found to aid the hinge effect and the opening of the two halves of disc 4 as hereinafter described. A support spine 6 extends opposite radial gap 14, operatively interconnecting disc 4 to bridge 8 for support. Two, symmetrically opposed, cleats 5, extend outward from disc 4 at approximately a 30° angle, symmetrically disposed such that it would be bisected by an imaginary line extending along radial gap 14 through pivot notch 7.

Within each of cleats 5 may be found forceps notch 28, adapted for operative engagement with a common forceps to permit the ready grasping of an actuation of the clamp section 4 as hereinafter described.

A cholangioclamp 1 is designed to facilitate the operative procedure of intraoperative cholangiography. The cholangioclamp 1 forms an occlusive seal around cystic duct 20 of gall bladder 22 after a No. 8 French catheter 2 has been introduced through a small flap cut in the cystic duct 20. X-rays are taken as dye is injected via the standard Leur lock into the catheter 2. The catheter 2 is forty centimeters long and protrudes from the clamp for two centimeters 13.

An occlusive seal is formed by the serrated clamp 4 which is five millimeters long and preferably provided with ten teeth 30, producing a pitch of 0.5 millimeters per tooth. The internal diameter 24 is 3.5 millimeters allowing for a typical 0.75 millimeter wall thickness 26 of the cystic duct 20 around the two millimeter diameter catheter 2. When the clamp is opened with clamp forceps (not shown), the gap 14 widens to allow the distal gall bladder 22 and cystic duct 20 to pass. When the forceps are removed, the clamp 4 springs shut around the hinge point 7. A lateral spine 6 supports the clamp 4 and is the axis about which the cleats 5 pivot. Activating forceps of typical design will fit snugly in opposing grooves 28 within each cleats 5 with the retaining brackets 10 and hold the clamp at a 30° angle 11 during application. The forceps are removed for x-rays.

A one centimeter support bridge 8 which is 120° in arc adds extra resilience to the hinge 7 for a firm occlusion and also provide a gap for the distal gall bladder 20, 22. This continues on to the mounting ring 9 which is slidingly affixed around catheter 2.

Figure 5:
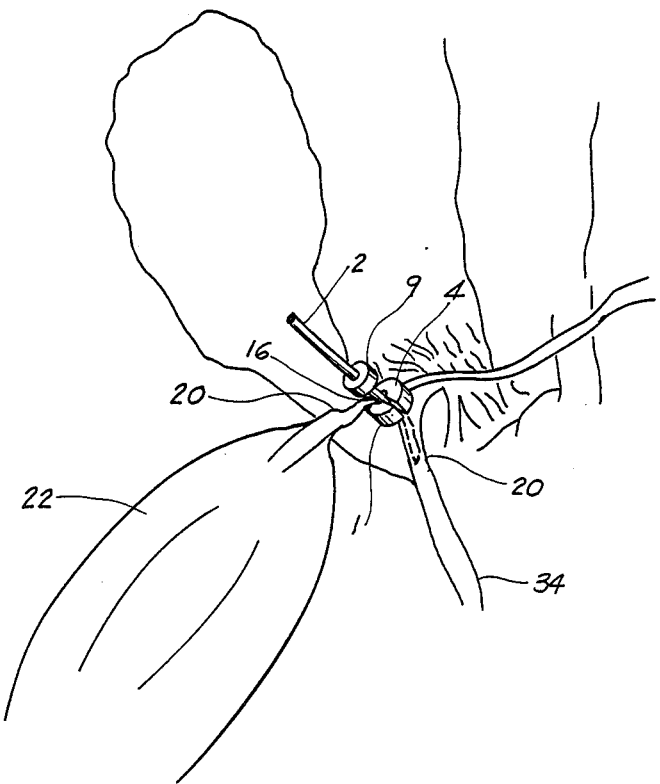
FIG. 5 is an illustrative depiction of a catheter being inserted within the cystic duct during the process of cholangiography, showing the relative orientation of the catheter, the clamp, and the duct.

FIG. 5 depicts the clamp 1 introduced onto the cystic duct 20 with the gall bladder 22 hanging out through the gap 16 of the clamp 1. X-rays are taken as dye is injected into the catheter tip 3 to watch for defects in the bile duct 34. The seal formed by clamp 4 will allow for enough pressure without spillage to observe dye running into the small bowel or to check for obstruction at the ampulla.

In order to illustrate the operative aspects and function of the clamp of the current invention, the preferred description has concentrated upon the field of cholangiography, which represents the preferred environment known to the inventor at this time for the clamp. However, it is obvious that the clamp has equal utility in any surgical environment in which it is necessary to secure a catheter temporarily to a tubular structure. Therefore, although such procedures are not here disclosed, their use should be obvious to those of ordinary skill in the art; it is suggested that the clamp would be of equal utility for such procedures as canalization of blood vessels and the like.

Therefore, the invention is not limited to the specific operative embodiment disclosed above but rather to that wider class of clamps as claimed.

I claim:

1. An apparatus for clamping a catheter insertably within a continuous structure comprising:
   a. Guide means, slidably enclosing said catheter, adapted for motion along a length of said catheter adjacent to tip thereof;

b. Beam support means extending outwardly from guide means in a direction towards said tip;

c. A split ring clamp means affixed at an end of said beam support means opposite said guide means comprising a first semi-cylindrical resilient clamping member extending from a point adjacent said support beam, encompassing a semi-circumferential section of said catheter;

d. A second, semi-cylindrical resilient clamping member extending from a point upon said support beam and opposing engagement to said first member encompassing a second semi-circumference of said catheter;

e. Means for deflecting said first and said second member from a position contactingly encompassing said catheter to a position apart from said catheter; and f. Means upon the interface of said first and said second members for establishing a sealing relationship between said members, said catheter, and an interposed tubular structure circumferentially surrounding said catheter;

2. The apparatus as described in claim 1 above wherein said sealing means further comprises a periodically ridged toothed structure extending inwardly from an inner surface of said first member and said second member.

* * * * *